US00PP35047P2

(12) United States Plant Patent
Nelson et al.

(10) Patent No.: US PP35,047 P2
(45) Date of Patent: Mar. 21, 2023

(54) STRAWBERRY PLANT NAMED 'FPS-14_552-008'

(50) Latin Name: ***Fragaria* x *ananassa***
Varietal Denomination: FPS-14_552-008

(71) Applicant: Fragaria Plant Sciences, B.V., Veldoven (NL)

(72) Inventors: Jonathan R. Nelson, Watsonville, CA (US); Daniel S. Nelson, Watsonville, CA (US); Scott C. Nelson, Watsonville, CA (US); Jeffrey D. Nelson, Watsonville, CA (US)

(73) Assignee: Fragaria Plant Sciences, B.V., Veldoven (NL)

( * ) Notice: Subject to any disclaimer, the term of this patent is extended or adjusted under 35 U.S.C. 154(b) by 0 days.

(21) Appl. No.: 17/886,422

(22) Filed: Aug. 11, 2022

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

(56) References Cited

U.S. PATENT DOCUMENTS

PP23,257 P2 12/2012 Nelson et al.

*Primary Examiner* — Susan McCormick Ewoldt
(74) *Attorney, Agent, or Firm* — Foley & Lardner LLP

(57) ABSTRACT

This invention relates to a new and distinct variety of strawberry plant named 'FPS-14_552-008'. This new strawberry plant named 'FPS-14_552-008' is primarily adapted to the growing conditions of the central coast of California, and is primarily characterized by its red fruit color, medium fruit size, and conical fruit shape; excellent fruit flavor, medium skin firmness, with seeds typically held even with the surface; very smooth fruit surface, even in color, with a slight difference in size between primary and secondary fruit; medium to large plant size, upright in habit with medium density; medium yellow green foliage color, and medium to large foliage size; and fruiting trusses typically held level with to below the plant, with medium to high pubescence.

5 Drawing Sheets

Latin name of the genus and species of the plant claimed: *Fragaria* x *ananassa.*

Variety denomination: 'FPS-14_552-008'.

BACKGROUND OF THE INVENTION

The present invention relates to a new and distinct strawberry variety named 'FPS-14_552-008'. This new variety is a result of a controlled cross made in 2014 in an ongoing breeding program between strawberry variety designated 'Sonata' as the seed (female) parent, and strawberry variety designated 'BG-4315' (U.S. Plant Pat. No. 23,257) as the pollen (male) parent. The variety is botanically known as *Fragaria* x *ananassa.*

The seedling resulting from the aforementioned cross was selected from a controlled breeding plot in Santa Cruz County, Calif. in the spring of 2016. After its selection, the new variety was asexually propagated by stolons in San Joaquin County, Calif. The new variety was tested extensively over the next several years in fruiting fields in Santa Cruz County, Calif. This propagation has demonstrated that the combination of traits disclosed herein as characterizing the new variety are fixed and remain true-to-type through successive generations of asexual reproduction.

BRIEF SUMMARY OF THE INVENTION

'FPS-14_552-008' is primarily adapted to the climate and growing conditions of the central coast of California. The nearby Pacific Ocean provides the humidity and moderate temperatures needed to produce a strong, vigorous plant and maintain fruit quality during the April through June production months.

The following traits have been repeatedly observed and are determined to be unique characteristics of 'FPS-14_552-008', which in combination distinguish this strawberry plant as a new and distinct variety:

1. Fruit is red in color, medium in size, and conical in shape;
2. Fruit has excellent flavor, medium skin firmness, with seeds typically held even with the surface;
3. Fruit surface is very smooth, even in color, with a slight difference in size between primary and secondary fruit;
4. Plant is medium to large in size, upright in habit with medium density;
5. Foliage is medium yellow green in color and medium to large in size; and
6. Fruiting trusses are typically held level with to below the plant, with medium to high pubescence.

The strawberry variety that is believed to be most closely related to the new variety 'FPS-14_552-008' is 'BG-4315' (U.S. Plant Pat. No. 23,257). In side-by-side comparisons to the similar strawberry variety 'BG-4315', 'FPS-14_552-008' differs by the following combination of characteristics as described in Table 1.

TABLE 1

| Characteristic | 'FPS-14_552-008' | 'BG-4315' (U.S. Plant Pat. No. 23,257) |
|---|---|---|
| Fruit: color | Red | Orange red |
| Fruit: Season average size (grams) | 21.0 | 26.9 |
| Terminal leaflet: shape of base | Obtuse | Acute |
| Terminal leaflet: margins (shape of teeth) | Obtuse (serrate to crenate) | Rounded (crenate) |
| Foliage: interveinal blistering | Medium to strong | Absent or weak |
| Petiole: Size (cm) | 20.2 | 15.8 |
| Plant: spread (cm) | 37.1 (large) | 25.2 (small) |
| Fruit: Flavor | Excellent | Fair to good |
| Flower: sepal color (upper surface) | Yellow green group (144B) | Green group (137B) |

For identification, a series of molecular markers have been determined for this new variety.

'FPS-14_552-008' differs from its parents, 'Sonata' and 'BG-4315' (U.S. Plant Pat. No. 23,257) by the following combination of characteristics as described in Tables 2 and 3.

TABLE 2

| Characteristic | 'FPS-14_552-008' | 'Sonata' |
|---|---|---|
| Fruit: color | Red | Orange red |
| Fruit: size | Medium to large | Small to medium |
| Fruit: flavor | Excellent | Fair |
| Plant: size | Large | Medium |

TABLE 3

| Characteristic | 'FPS-14_552-008' | 'BG-4315' (U.S. Plant Pat. No. 23,257) |
|---|---|---|
| Plant: type | June bearer | Short day |
| Fruit: firmness of flesh | Medium | Firm |
| Fruit: flavor | Excellent | Fair |
| Plant: size | Large | Small to medium |

BRIEF DESCRIPTIONS OF THE PHOTOGRAPHS

The accompanying color photographs illustrate the overall appearance of typical specimens of the new strawberry variety 'FPS-14_552-008' at various stages of development, as true as it is reasonably possible with color reproductions of this type. Color in the photographs may differ slightly from the color value cited in the botanical descriptions which accurately describe the color of 'FPS-14_552-008'. The depicted plant and plant parts of the new strawberry variety 'FPS-14_552-008' are approximately three to four months old. The photographs were taken in Santa Cruz County, Calif.

DETAILED BOTANICAL DESCRIPTION

Figure 1:
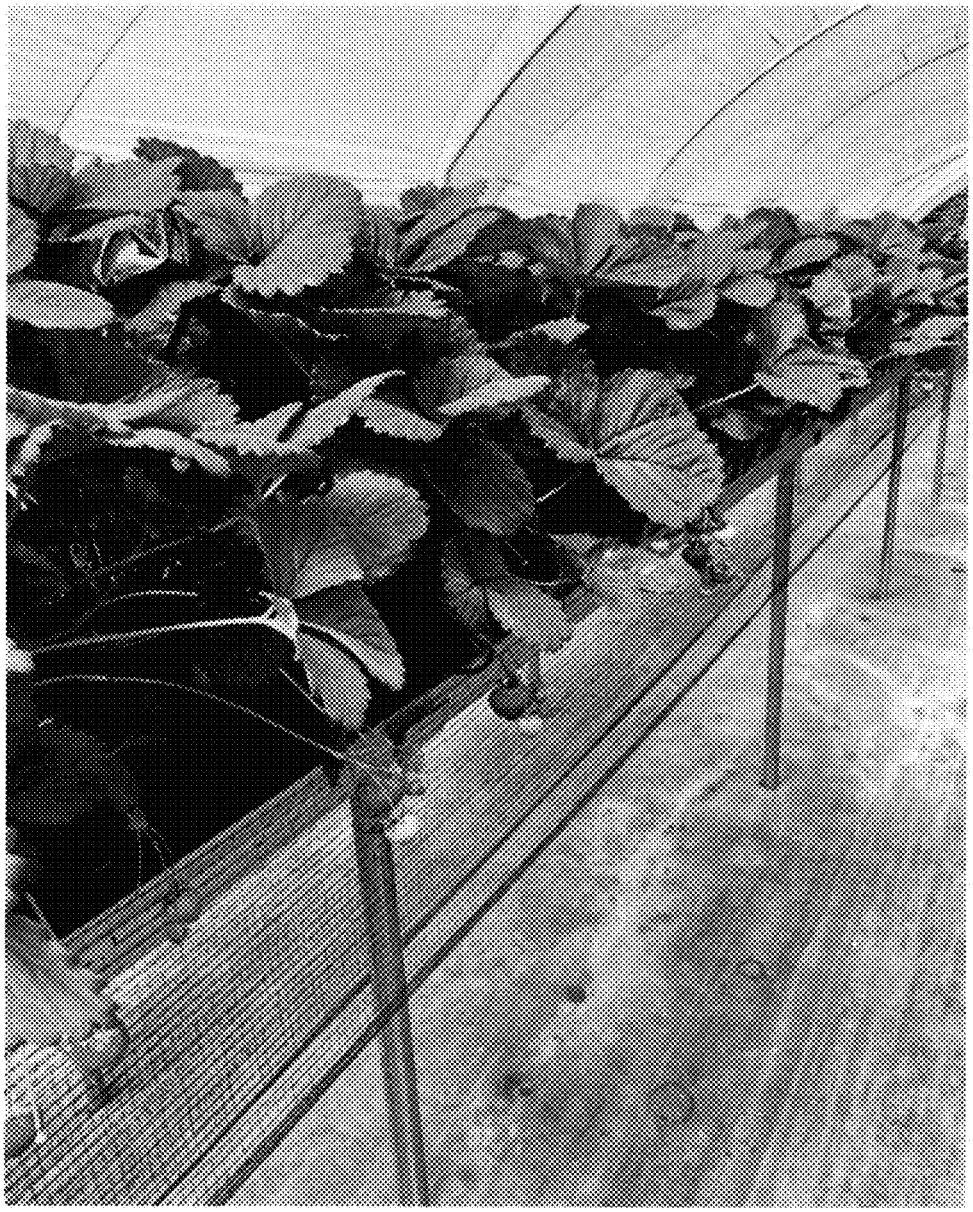
FIG. 1 shows fruiting field characteristics of 'FPS-14_552-008', taken in the month of June 2022.
Figure 2:
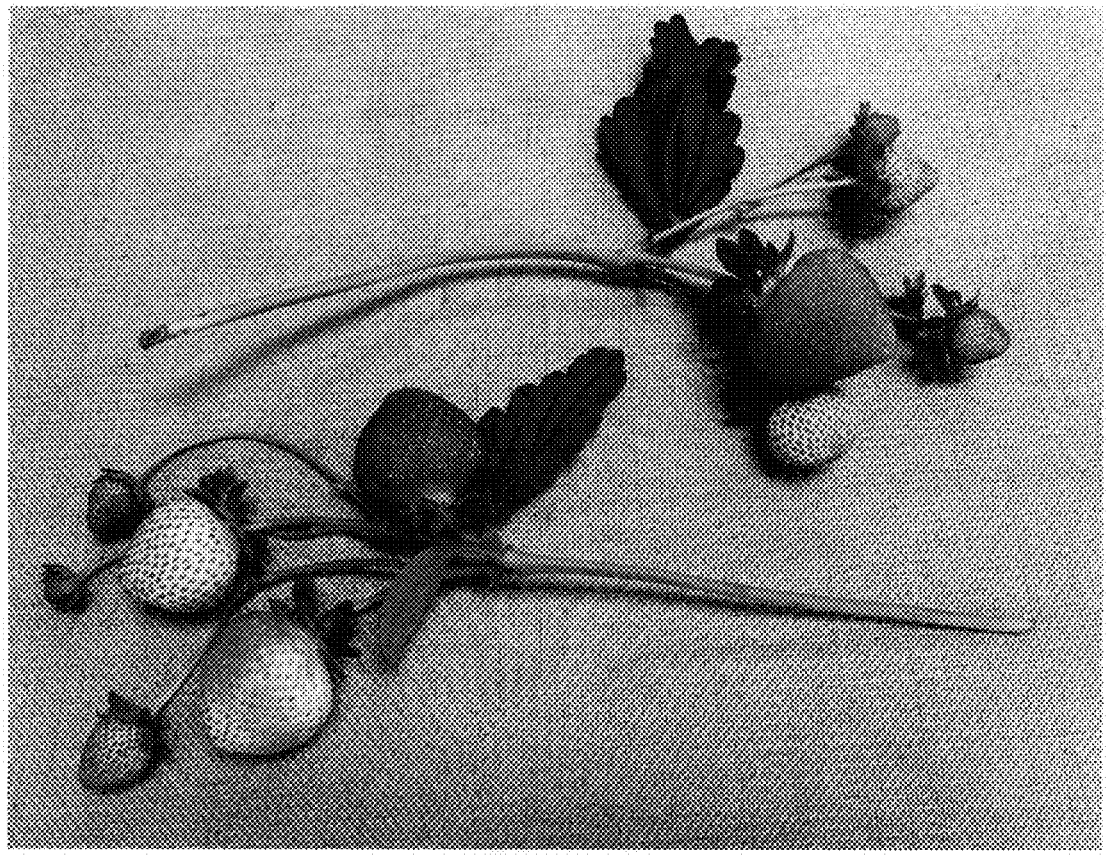
FIG. 2 shows typical fruiting truss and truss parts of 'FPS-14_552-008', taken in the month of June 2022.
Figure 3:
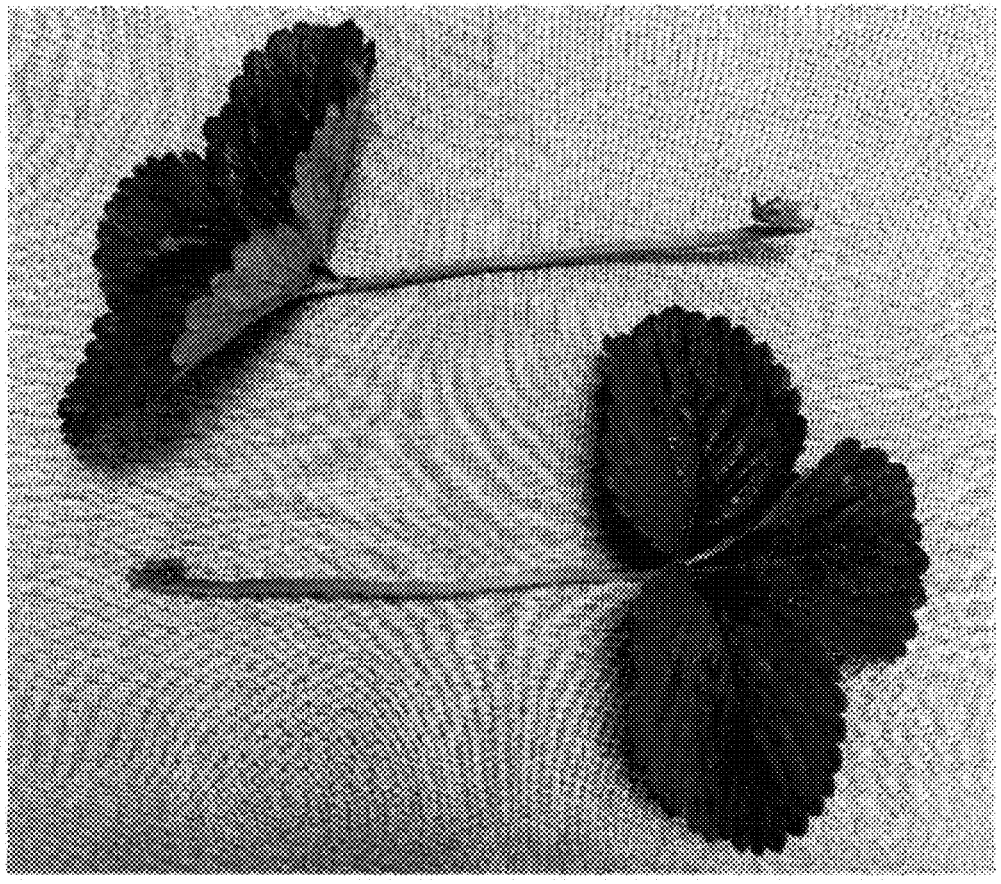
FIG. 3 shows upper and lower surfaces of leaf and leaf parts of 'FPS-14_552-008', taken in the month of June 2022.
Figure 4:
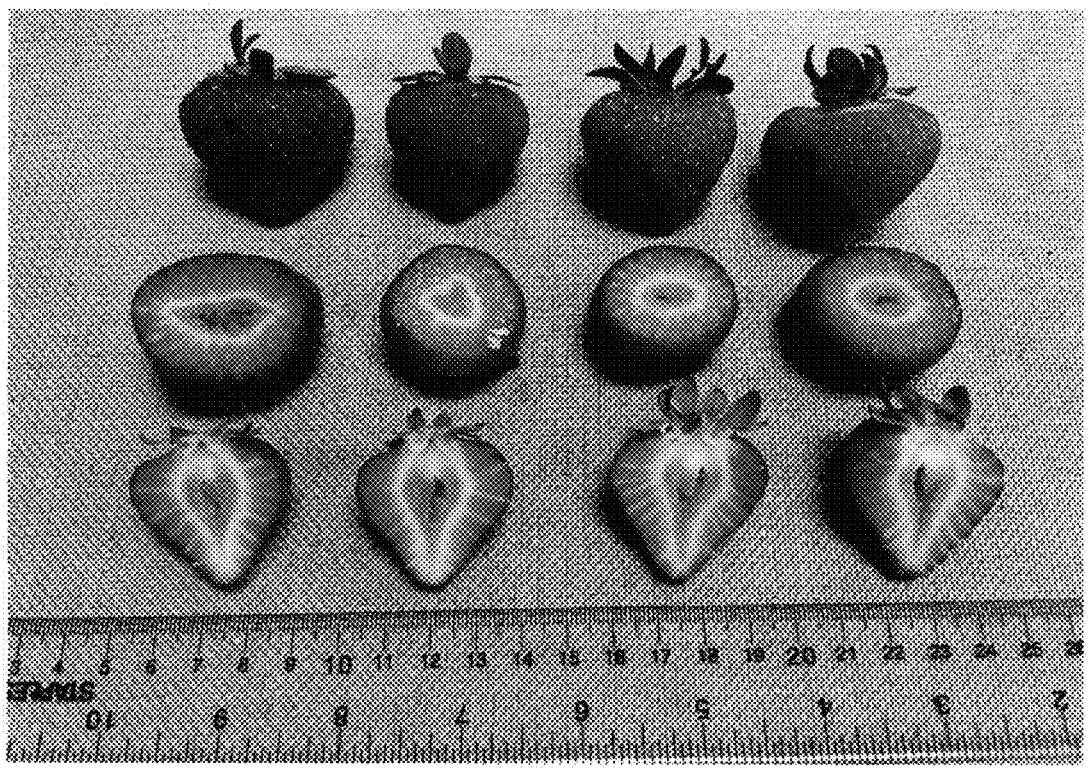
FIG. 4 shows internal and external mature fruit characteristics of 'FPS-14_552-008', taken in the month of June 2022.
Figure 5:
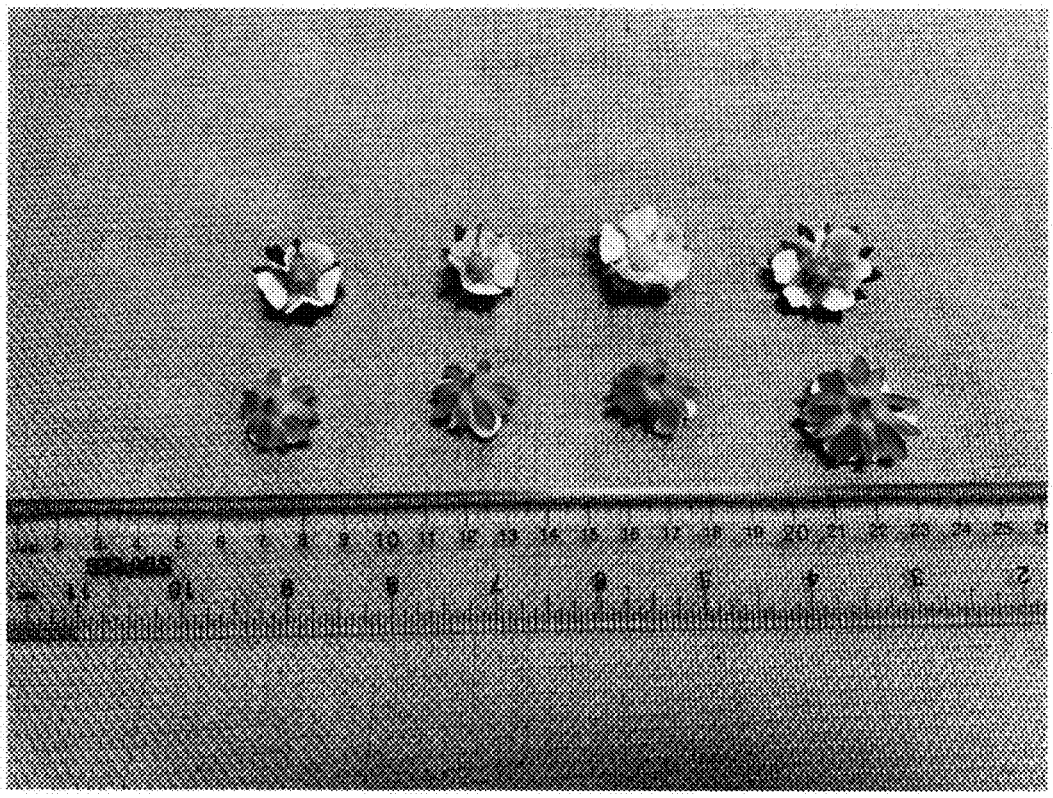
FIG. 5 shows upper and lower surfaces of flower and flower parts of 'FPS-14_552-008', taken in the month of July 2022.

The new variety 'FPS-14_552-008' has not been observed under all possible environmental conditions. The characteristics of the new variety 'FPS-14_552-008' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'FPS-14_552-008', unless otherwise noted, are based on observations taken during the 2022 growing season in Santa Cruz County, Calif. These measurements and ratings were taken from plants of 'FPS-14_552-008' dug from a low-elevation nursery located in San Joaquin County, Calif. in December 2021 and planted approximately two months later in Santa Cruz County, Calif. The approximate age of the observed plants is three to four months. Yield observations including average weight and marketable yield, along with fruit quality characteristics including soluble solids, are averaged from five years of data collected from the 2018 through 2022 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'FPS-14_552-008'.

Fruit characteristics:

*Color of mature fruit*.—RHS 45A (red).
*Color of internal flesh*.—RHS 44A (medium red).
*Color of core*.—RHS 39A (light red).
*Average length* (*cm*).—4.1.
*Average width* (*cm*).—3.7.
*Size*.—Medium.
*Average length/width ratio*.—1.11 (ranges from slightly broader than long to as long as broad).
*Hollow center average length* (*mm*).—2.4.
*Hollow center average width* (*mm*).—1.4.
*Hollow center expression*.—Absent or very weak.
*Season average weight* (*gm*).—21.0.
*Marketable yield season* (*gm/plant*).—360.
*Predominant shape*.—Conical.
*Difference in shape between primary and secondary fruit*.—Slight.
*Band without achenes*.—Ranges from narrow to medium.
*Evenness of surface*.—Even or very slightly uneven.
*Evenness of color*.—Even or very slightly uneven.
*Glossiness*.—Strong.
*Insertion of achenes*.—Level with surface.
*Average calyx diameter* (*cm*).—2.8.

*Position of calyx attachment*.—Level.
*Attitude of sepals*.—Outward.
*Size of calyx in relation to fruit diameter*.—Ranges from slightly smaller to same size.
*Adherence of calyx* (*when fully ripe*).—Strong.
*Firmness of flesh*.—Ranges from medium to firm.
*Keeping quality*.—Ranges from good to moderate.
*Fruit market*.—Fresh.
*Post-harvest fruit longevity* (*at* 1 *to* 3 *degrees Celsius*).—Moderate to fair (5 to 7 days).
*Distribution of red color of the flesh*.—Marginal and central.
*Flavor*.—Excellent.
*Soluble solids* (*% Brix*).—7.0.
*Achene color, shaded side*.—RHS 153C (yellow green group).
*Achene color, sun-exposed side*.—RHS 180C (greyed purple group).
*Achene average length* (*mm*).—1.4.
*Achene average width* (*mm*).—1.1.
*Achene average weight* (*mg*).—0.48.
*Achene average quantity per berry*.—242.
*Achene shape*.—Ovate.

Time of flowering:
*Flowering season* (50% *of plants with at least one flower*).—Medium (April in Santa Cruz County, Calif.).
*Maturing season* (50% *of plants with mature fruit*.—Medium (May in Santa Cruz County, Calif.).
*Flowering season*.—April through June (in Santa Cruz County, Calif.).
*Harvest season*.—April through June (in Santa Cruz County, Calif.).
*Harvest maturity*.—Early to mid-season (April through June).
*Plant hardiness*.—Zone 9 (USDA Plant Hardiness Zone Map).
*Type of bearing*.—Not remontant.

Plant characteristics:
*Average height* (*cm*).—28.9.
*Average spread* (*cm*).—37.1.
*Average crowns per plant*.—3.5.
*Size*.—Large.
*Habit*.—Ranges from semi-upright to spreading.
*Density*.—Ranges from medium to dense.
*Vigor*.—Ranges from medium to strong.

Stolon characteristics:
*Color*.—RHS 144C (yellow green group).
*Anthocyanin coloration*.—RHS 182B (greyed red group).
*Anthocyanin intensity*.—Ranges from weak to medium.
*Pubescence*.—Ranges from medium to dense.
*Attitude of hairs*.—Upward.
*Average quantity in nursery* (*per square foot*).—4 to 5 (medium).
*Average diameter at first bract* (*mm*).—4.1 (thick).
*Length from mother plant to first daughter* (*cm*).—26.7.

Terminal leaflet characteristics:
*Average length* (*cm*).—9.3.
*Average width* (*cm*).—8.1.
*Average area terminal* ($cm^2$).—75.3.
*Average length/width ratio*.—1.14 (longer than broad).
*Shape of base*.—Obtuse.
*Shape of apex*.—Obtuse.
*Margins* (*shape of teeth*).—Obtuse (serrate to crenate).
*Average serrations per leaf*.—21.8.

Foliage characteristics:
*Color of upper surface*.—RHS 141B (dark yellow green).
*Color of lower surface*.—RHS 147C (yellow green group).
*Color of venation, upper surface*.—RHS 151B (yellow green group).
*Color of venation, lower surface*.—RHS N144B (yellow green group).
*Number of leaflets*.—3.
*Leaf size*.—Ranges from large to medium.
*Average length* (*cm*).—9.3.
*Average width* (*cm*).—19.1.
*Average area foliage* ($cm^2$).—178.4.
*Shape in cross section*.—Ranges from slightly concave to flat.
*Interveinal blistering*.—Ranges from medium to strong.
*Texture of upper surface*.—Ranges from smooth to medium.
*Texture of lower surface*.—Smooth.
*Venation pattern*.—Pinnate reticulate.
*Leaf glossiness*.—Ranges from absent or weak to medium.
*Leaf variegation*.—Absent.

Petiole characteristics:
*Petiole color*.—RHS 144B (yellow green group).
*Petiole average length* (*cm*).—20.2.
*Petiole average diameter* (*mm*).—4.2.
*Attitude of hairs*.—Strongly outward.
*Frequency of bract leaflets*.—0% (none).
*Size of bract leaflets*.—N/A.
*Pubescence*.—Ranges from heavy to moderate.
*Petiolule color*.—RHS 144B (yellow green group).
*Petiolule average length* (*mm*).—5.1.
*Petiolule average diameter* (*mm*).—2.0.

Stipule characteristics:
*Color*.—RHS 145A (yellow green group).
*Anthocyanin coloration*.—RHS 58A (red purple group).
*Anthocyanin intensity*.—Strong.
*Average length* (*mm*).—24.2.
*Average width* (*mm*).—8.5.
*Shape*.—Triangular.
*Texture*.—Light.
*Shape of base*.—N/A.
*Shape of apex*.—Acute.
*Margins*.—Entire (smooth).

Fruiting truss characteristics:
*Anthocyanin coloration*.—RHS 182B (greyed red group).
*Anthocyanin intensity*.—Absent or very weak.
*Average length at maturity* (*cm*).—17.3.
*Position relative to foliage*.—Beneath.
*Flower quantity* (*season average per plant*).—20 (medium).
*Average fruit quantity per truss*.—5.3 (medium).
*Attitude at first pick*.—Prostrate.
*Primary pedicel color*.—RHS 144B (yellow green group).
*Primary pedicel average length* (*cm*).—4.4.
*Primary pedicel average diameter* (*mm*).—2.4.
*Pedicel attitude of hairs*.—Upward.
*Pedicel texture*.—Weak.

*Primary peduncle color*.—RHS 144B (yellow green group).
*Primary peduncle average length* (*cm*).—17.5.
*Primary peduncle average diameter* (*mm*).—4.0.
*Peduncle texture*.—Weak.

Flower characteristics:
*Petal color, upper surface*.—RHS 155C (white group).
*Petal color, lower surface*.—RHS 155C (white group).
*Petal average length* (*mm*).—10.1.
*Petal average width* (*mm*).—9.9.
*Petal average length/width ratio*.—1.02 (as long as broad).
*Average petal quantity per flower*.—7.1.
*Petal shape*.—Rounded.
*Petal texture, upper surface*.—Smooth.
*Petal texture, lower surface*.—Smooth.
*Petal shape of base*.—Acute.
*Petal shape of apex*.—Rounded.
*Petal margins*.—Entire (smooth).
*Sepal color, upper surface*.—RHS 144B (yellow green group).
*Sepal color, lower surface*.—RHS 144B (yellow green group).
*Sepal average length* (*mm*).—7.6.
*Sepal average width* (*mm*).—4.2.
*Sepal average length/width ratio*.—1.8.
*Average sepal quantity per flower*.—13.
*Sepal shape*.—Elliptical.
*Sepal texture, upper surface*.—Ranges from smooth to light.
*Sepal texture, lower surface*.—Ranges from smooth to light.
*Sepal shape of apex*.—Acute.
*Sepal margins*.—Entire (smooth).
*Flower bud color*.—RHS 145A (yellow green group).
*Flower bud shape*.—Bell.
*Flower bud average length* (*mm*).—13.8.
*Flower bud average diameter* (*mm*).—7.5.
*Corolla average diameter* (*mm*).—24.1 (medium).
*Flower average depth* (*mm*).—9.6 (ranges from shallow to medium).
*Calyx average diameter* (*mm*).—27.8.
*Size of calyx relative to corolla*.—Larger.
*Relative position of petals* (*flowers with* 5 *or* 6 *petals*).—Overlapping.
*Size of inner calyx relative to outer calyx*.—Smaller.

Reproductive organs:
*Anther color*.—RHS 13A (yellow group).
*Filament color*.—RHS 145C (yellow green group).
*Filament average length* (*mm*).—2.1.
*Anther average length* (*mm*).—1.8.
*Anther average width* (*mm*).—1.0.
*Anther shape*.—Broad elliptic.
*Pollen amount*.—Abundant.
*Ovary color*.—RHS 147C (yellow green group).
*Style color*.—RHS 151C (yellow green group).
*Pistil average quantity per flower*.—350.
*Pistil average length* (*mm*).—1.0.
*Style average length* (*mm*).—1.1.
*Stigma average diameter* (*mm*).—0.2.
*Stigma shape*.—Rounded.

Disease and pest reactions:
*Powdery mildew* (*Sphaerotheca macularis*).—Moderately resistant.
*Angular leaf spot* (*Xanthomonas fragariae*).—Ranges from moderately resistant to moderate.
*Botrytis fruit rot* (*Botrytis cinerea*).—Moderately susceptible.
*Fusarium wilt* (*Fusarium oxysporum*).—Resistant.
*Anthracnose crown rot* (*Colletotrichum fragariae*).—Unknown.
*Two-spotted spider mite* (*Tetranychus urticae*).—Unknown.

We claim:

1. A new and distinct strawberry plant named 'FPS-14_552-008', as herein described and illustrated by the characteristics set forth above.

* * * * *